(12) United States Patent
Dierking et al.

(10) Patent No.: US 8,252,315 B2
(45) Date of Patent: Aug. 28, 2012

(54) HYPOALLERGENIC COMPOSITION

(75) Inventors: Mark Dierking, Topeka, KS (US);
Dennis Edward Jewell, Lawrence, KS (US); Luis Jose Montelongo, Lawrence, KS (US); Fernando Qvyjt, Topeka, KS (US); Naina Kiran Shah, Lawrence, KS (US); Timothy Glen Vande Giessen, Topeka, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 182 days.

(21) Appl. No.: 12/262,342

(22) Filed: Oct. 31, 2008

(65) Prior Publication Data

US 2009/0054301 A1 Feb. 26, 2009

Related U.S. Application Data

(62) Division of application No. 10/996,223, filed on Nov. 23, 2004.

(51) Int. Cl.
*A23K 1/17* (2006.01)
*A23L 3/015* (2006.01)

(52) U.S. Cl. ......... 424/442; 426/665; 426/804; 426/805

(58) Field of Classification Search .................. None
See application file for complete search history.

(56) References Cited

U.S. PATENT DOCUMENTS

| | | |
|---|---|---|
| 2,566,549 A | 9/1951 | Beckwith et al. |
| 3,394,016 A | 7/1968 | Bidmead et al. |
| 3,898,345 A | 8/1975 | Horrocks et al. |
| 4,216,237 A | 8/1980 | Smith |
| 4,444,796 A * | 4/1984 | Ueno et al. ............. 426/335 |
| 4,471,001 A | 9/1984 | Lynch |
| 4,879,131 A | 11/1989 | de Rahm |
| 4,981,704 A | 1/1991 | Thibault |
| 5,039,532 A | 8/1991 | Jost et al. |
| 5,405,637 A | 4/1995 | Martinez et al. |
| 5,589,357 A | 12/1996 | Martinez et al. |
| 5,928,686 A | 7/1999 | Ivey et al. |
| 6,403,142 B1 | 6/2002 | McDaniel, III et al. |
| 6,455,273 B1 | 9/2002 | Kodera et al. |
| 6,589,574 B2 | 7/2003 | Swamylingappa et al. |
| 6,783,792 B2 | 8/2004 | McDaniel, III et al. |
| 2003/0035882 A1 | 2/2003 | McDaniel et al. |
| 2003/0059517 A1 | 3/2003 | McDaniel, III et al. |
| 2003/0072786 A1 * | 4/2003 | Hayek et al. ............. 424/442 |
| 2003/0124239 A1 | 7/2003 | Kelleher |
| 2003/0170373 A1 | 9/2003 | LeBlanc |

FOREIGN PATENT DOCUMENTS

| | | |
|---|---|---|
| EP | 189161 A2 * | 7/1986 |
| EP | 0189161 | 7/1991 |
| EP | 1236405 A1 * | 9/2002 |
| JP | 06-157233 | 6/1994 |
| JP | 10-203994 | 8/1998 |
| JP | 2001-333794 | 12/2001 |
| WO | WO 00/30456 | 6/2000 |
| WO | WO 02/086102 | 10/2002 |
| WO | WO 2004/049818 | 6/2004 |
| WO | WO 2004/060080 | 7/2004 |
| WO | WO 2006/036766 | 4/2006 |

OTHER PUBLICATIONS

FDA Article "Pet Food Labels—General" accessed online on Mar. 25, 2011 at <https://www.fda.gov/animalveterinary/resourcesforyou/ucm047113.htm>. See parent U.S. Appl. No. 10/996,223 for reference.*
Britten et al., "Effect of pH During Heat Processing of Partially Hydrolyzed Whey Protein," J of Dairy Science, 77:676-684, 1994.
Cave NJ et al., "In vivo assessment of antigenicity of a protein hydrolysate and characterization of a major anitgen in chicken," ACVIM Abstract, 2000, Paper No. 147.
Cave NJ, et al. "A method for in vitro evaluation of protein hydrolysates for potential inclusion in veterinary diets," Res. Vet. Sci. 2004, 77(3):231-238.
FDA Article "Pet Food Labels—General" accessed online on Mar. 25, 2011 at <http://www.fda.gov/animalveterinary/resourcesforyou/ucm047113.htm>.
Husby, "Nutritional and Feeding Value of a Salmon Protein Hydrolysate in Diets for Weanling Pigs," Final Report, Alaska Fisheries Development Foundation, Feb. 1991.
Leksrisompong et al., "Characterization of Flavor of Whey Protein Hydrolysates," J. Agric. Food Chem., Apr. 23, 2010.
Neklyudov et al., "Properties and Uses of Protein Hydrolysates," Applied Biochemistry and Microbiology, 36(5): 452-459, 2000.
Olson ME et al., "Hypersensitivity reactions to dietary antigens in atopic dogs," Recent Advances in Canine and Feline Nutrition vol. III 2000, Iams Nutrition Symposium Proceedings, pp. 69-77.
Rosenberg, "Effects of Protein Aggregates: An Immunologic Perspective," AAPS Journal, 8(3): E501-E507, 2006.
Roudebush, P. "Adverse reactions to food [allergies]," Tijdschr Diergeneeskd., 1993, 118(Suppl 1): 29S-32S.
Roudebush, P. "Evaluation of a commercial canned lamb and rice diet for the management of adverse reactions to food in dogs," Vet. Dermatol., 1994, 5:3-67.
Roudebush, P. "Ingredients associated with advers food reactions in dogs and cats," adv. Sm. An. Med. Surg., 2002, 15(9):1-3.

* cited by examiner

*Primary Examiner* — Carlos Azpuru
*Assistant Examiner* — Casey Hagopian
(74) *Attorney, Agent, or Firm* — Michael F. Morgan

(57) ABSTRACT

This invention is directed generally to compositions (including foods, supplements, treats, toys, etc.) for animal (including pet) consumption, and particularly hypoallergenic compositions, and more particularly semi-solid hypoallergenic compositions and hypoallergenic compositions that comprise a hydrolysate. This invention also is directed generally to methods for using such compositions. This invention is further directed generally to processes for making such compositions.

2 Claims, No Drawings

HYPOALLERGENIC COMPOSITION

This application is a divisional of U.S. patent application Ser. No. 10/996,223 filed Nov. 23, 2004 which is a non-provisional of U.S. Provisional Application No. 60/612,661, filed on Sep. 24, 2004 the contents of which are incorporated herein by reference in their entirety for all purposes.

FIELD OF THE INVENTION

This invention is directed generally to compositions (including foods, supplements, treats, toys, etc.) for animal (including pet) consumption, and particularly hypoallergenic compositions, and more particularly semi-solid hypoallergenic compositions and hypoallergenic compositions that comprise a hydrolysate. This invention also is directed generally to methods for using such compositions. This invention is further directed generally to processes for making such compositions.

BACKGROUND OF THE INVENTION

Mammals, including companion animals (e.g., dogs and cats), can be afflicted with allergies to foods. In some cases, the caretaker of an afflicted companion animal attempts to mitigate the animal's food allergy symptoms by placing the animal on a restricted diet that reduces or excludes a food allergen(s). In response to demand for pet food compatible with an allergen-restricted diet, some commercial pet food manufacturers have developed hypoallergenic pet foods. Some such foods have been sold in solid or "dry food" formats such as kibbles. These hypoallergenic pet foods can be unpalatable to or inappropriate for certain companion animals. Such dry foods can be undesirable to a pet owner for a variety of other reasons as well.

SUMMARY OF THE INVENTION

This invention is directed to compositions for animal (e.g., pet) consumption, particularly hypoallergenic compositions. It is contemplated that such compositions may be suitable for use with a variety of mammalian and non-mammalian animals.

Briefly, therefore, this invention is directed, in part, to a hypoallergenic composition for animal consumption (particularly for pet consumption), such as, for example, a food, nutritional supplement, treat, or toy. The composition comprises a hydrolysate.

In one such embodiment, for example, the composition comprises a semi-solid formulation.

This invention also is directed to an animal treat. The treat is hypoallergenic and comprises hydrolysate.

This invention also is directed to an animal toy. The toy is hypoallergenic and comprises hydrolysate.

This invention also is directed to processes for preparing such compositions, treats, and toys.

This invention also is directed to methods for using such compositions, treats, and toys.

Further benefits of Applicants' invention will be apparent to one skilled in the art from reading this patent.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

It is contemplated that the compositions and methods of this invention may be useful for a variety of mammals, including non-human mammals such as non-human primates (e.g., monkeys, chimpanzees, etc.), companion animals (e.g., dogs, cats, equine, etc.), farm animals (e.g., goats, sheep, swine, bovine, etc.), laboratory animals (e.g., mice, rats, etc.), and wild and zoo animals (e.g., wolves, bears, deer, etc.).

In some embodiments of this invention, the animal is a carnivorous mammal, i.e., a meat-eating mammal.

In some embodiments of this invention, the animal is an omnivorous mammal, i.e., a mammal that eats both plants and meat.

In some embodiments of this invention, the animal is a companion animal.

In some embodiments of this invention, the animal is a cat.

In some embodiments of this invention, the animal is a dog.

In accordance with this invention, Applicants have developed pet foods that are hypoallergenic to companion animals and are in semi-solid formulations.

These compositions comprise a hydrolysate, which can serve as a hypoallergenic nutritional source of protein, polypeptides and/or amino acids for a companion animal diet.

In various embodiments, a hypoallergenic pet food can comprise a composition comprising a hydrolysate in an acceptable, semi-solid formulation. In some configurations, a hydrolysate comprised by a hypoallergenic pet food described herein can be a frozen hydrolysate, a freshly prepared hydrolysate or a hydrolysate that is stored refrigerated before use. Furthermore, a hydrolysate comprised by a hypoallergenic pet food described in various configurations herein can be a hydrolysate prepared by a method comprising freezing the hydrolysate, vacuum drying the hydrolysate, spray drying the hydrolysate, drum drying the hydrolysate or freeze drying the hydrolysate. In some configurations, the hydrolysate can be prepared by a method which comprises freezing the hydrolysate.

In various embodiments, a hypoallergenic pet food can comprise a composition which is acceptable to both a pet animal and the pet's caregiver. The acceptability of a pet food composition in the various embodiments of the present invention includes organoleptic acceptability to the animal, which can be measured, for example, by determining the average amount of the composition consumed by test animals in a consumption test. A composition is considered, herein, to be organoleptically acceptable if the average amount consumed by test animals in a consumption test provides nutrients in at least a nutritionally sufficient amount. Acceptability can also include, in certain aspects, attractiveness of a composition to a pet caretaker such that the caretaker can be favorably disposed towards offering the composition to the pet. In addition, an acceptable composition can be a composition which does not comprise components which are toxic or not generally regarded as safe for consumption by a pet animal.

In various embodiments, an organoleptically acceptable pet food can be a pet food which is palatable to a pet animal. A palatable hypoallergenic pet food of these embodiments can be a pet food in a format such as, without limitation, a semi-solid format, a liquid format, for example a slurry, a gravy, a gel, a hash, a purée, or a semi-moist pet food formulation format, but not a gruel. Organoleptic acceptability or palatability, in these embodiments, can be determined by testing consumption by animals under standardized conditions in a palatability test. In one palatability test, a plurality of test animals are offered a choice between a test hypoallergenic pet food having a composition disclosed herein, and a comparator diet comprising a pet food of known composition, under test conditions described below. An intake ratio (IR), defined as the average ratio of test pet food ingested to total pet food ingested, can be determined for a test formulation. In various configurations, a hypoallergenic pet food of the present teachings can yield an IR of at least about 0.20, at least about 0.25, at least about 0.3, at least about 0.4, at least about 0.5, or greater.

In a second test, palatability of a hypoallergenic pet food of the present teachings can be determined by measuring average intake by test animals under standardized conditions. In some configurations, the average amount of intake can be an amount which provides at least sufficient calories for a pet animal's nutritional needs, which can be determined by the animal's size. In certain aspects, a palatable hypoallergenic pet food described herein can be a hypoallergenic canine pet food which can be ingested by a canine in an amount sufficient to provide a minimum daily caloric intake of at least about 63 times metabolic body size, defined herein as weight in kilograms raised to the 0.75 power. In certain other aspects, a palatable hypoallergenic pet food described her in can be a hypoallergenic feline pet food which can be ingested by a feline in an amount sufficient to provide a minimum daily caloric intake of at least about 56 times metabolic body size, defined by weight in kilograms raised to the 0.75 power. In various embodiments, the hypoallergenic pet foods described herein can have a water content greater than that of solid format pet foods such as kibbles. In various embodiments, a pet food composition can have a water content of at least about 15% by weight percentage (by weight), at least about 20% by weight, at least about 40% by weight, or at least about 60% by weight, to about 80% by weight. In some configurations, the water content can be from about 50% by weight to about 85% by weight or from about 75% by weight to about 78% by weight.

In various embodiments, a hypoallergenic pet foods can comprise a composition comprising a hydrolysate in an amount of from at least about 0.5% by weight to about 85% by weight on a dry matter basis. In some configurations, the hydrolysate content of a hypoallergenic pet food can be at least about 4% by weight to about 70% by weight, at least about 4% by weight to about 14% by weight, at least about 6% by weight to about 14% by weight, or at least about 25% by weight to about 85% by weight on a dry matter basis.

In certain configurations, a hypoallergenic pet food can comprise a shelf-stable composition. In various configurations, a hypoallergenic pet food can be a pet food intended for felines or a pet food intended for canines.

In certain embodiments of the present teachings, a hypoallergenic pet food composition can comprise a hydrolysate which comprises polypeptides and free amino acids in which about 60% to about 95% of the polypeptides and free amino acids have a molecular weight below about 15,000 Daltons, below about 12,000 Daltons, below about 10,000 Daltons. More preferably, from about 60% to about 95% of the polypeptides and free amino acids of the hydrolysate are characterized as having a molecular weight of less than about 8,000 Daltons, even more preferably less than about 6000 Daltons. In some aspects, the assemblage of polypeptides and free amino acids comprised by a hydrolysate can have a weighted average molecular weight of about 2,000 Daltons, about 4,000 Daltons, about 6,000 Daltons, about 12,000 Daltons, or about 18,000 Daltons. In various aspects, the hydrolysate can be a plant hydrolysate, or an animal hydrolysate. A plant hydrolysate can be, without limitation, a hydrolysate of protein obtained from edible tissue of a grain, a fruit, a root, a tuber, a stem, a leaf, or a vegetable. An animal hydrolysate can be, without limitation, a hydrolysate of protein obtained from tissue of a mammal, a fish, a bird, a reptile, an amphibian, or an invertebrate.

In various configurations of the present teachings, a hypoallergenic pet food can comprise, in addition to a hydrolysate and water, one or more nutritional supplements. These nutritional supplements can, in some configurations, modify the physical characteristics of a pet food, such as, for example, the pet food's firmness, flavor or texture. A nutritional supplement can be, in non-limiting example, a monosaccharide, a disaccharide, an oligosaccharide, a starch, a flour, a cellulose, a tuber, a grain selected from rice, wheat, corn and rye, a vitamin selected from vitamin A, vitamin C, vitamin D, vitamin E, vitamin K, thiamin, riboflavin, niacin, vitamin $B_6$, folic acid, vitamin $B_{12}$, biotin, and pantothenic acid, taurine, DL-methionine, a flavoring, and a mineral selected from dicalcium phosphate, potassium chloride, calcium carbonate, sodium chloride, potassium chloride, choline chloride, magnesium oxide, zinc oxide, ferrous sulfate, manganese oxide, copper sulfate, calcium iodate, and sodium selenium.

Hypoallergenic pet food compositions of the present teachings can include both "low allergen" and "ultra-low allergen" configurations. The latter can include hydrolysate as the source of at least about 95% of protein nutrition, at least about 99% of protein nutrition, or 100% of protein nutrition, while the former can include, in addition to hydrolysate, some non-hydrolyzed protein of low allergenicity, such as, for example, plant protein such as soy bean protein.

A hypoallergenic pet food composition of the present teachings can be, in various embodiments, a pet food composition that can be provided to a consumer in packaging. The packaging can be air-tight packaging, such as, in some configurations, a metal can.

In some embodiments, the present teachings include methods of making a hypoallergenic pet food composition. The hypoallergenic pet food composition that can be made using the methods can be, in various configurations, a semi-solid composition, a liquid composition, a paste composition, or a slurry composition. A method of making a hypoallergenic pet food composition in these embodiments can comprise forming a semi-solid mixture comprising a hydrolysate, and at least about 15% by weight water. The hydrolysate can be, in various aspects, a liquid hydrolysate, a frozen hydrolysate, or a dried hydrolysate. In various configurations, prior to forming the mixture, a method can further comprise freezing a liquid hydrolysate, vacuum drying a hydrolysate, spray drying a hydrolysate, drum drying a hydrolysate, or freeze drying the hydrolysate. In some configurations, the hydrolysate can be a frozen hydrolysate. In various aspects, the methods can include cutting, chopping, or grinding solid components of the composition such as the frozen hydrolysate, with or without liquid components present. In certain aspects, forming a mixture can comprise combining the components of the mixture. In various configurations, a method can comprise forming a mixture comprising at least about 15% by weight water, at least about 40% by weight water, at least about 50% by weight water, or to about 85% by weight water. In various configurations, components can be mixed together to form a mixture.

In various configurations, a mixture can comprise a hydrolysate in an amount of from at least about 0.5% by weight, to about 85% by weight, at least about 5% by weight to about 70% by weight, at least about 4% by weight to about 14% by weight, at least about 6% by weight to about 14% by weight, or at least about 55% by weight to about 65% by weight.

In various embodiments, the present teachings provide methods of improving the palatability of a hypoallergenic pet food composition. These methods can comprise preparing the pet food composition with a frozen hydrolysate. In these embodiments, the improved palatability can be palatability compared to that of an identical composition prepared with a dried hydrolysate. These methods can further comprise preparing the pet food composition with at least about 15% by weight water. The amounts of the frozen hydrolysate and the water can be the same as those of other embodiments described herein. Furthermore, various configurations of these methods can further comprise preparing the pet food composition with one or more of the nutritional supplements described in embodiments herein.

In various embodiments, a method of making a hypoallergenic semi-solid pet food composition can further comprise adding to the mixture one or more nutritional supplements. Some non-limiting nutritional supplements can be a monosaccharide, a disaccharide, an oligosaccharide, a starch, a flour, a cellulose, a tuber, a grain selected from rice, wheat, corn and rye, a vitamin selected from vitamin A, vitamin C, vitamin D, vitamin E, vitamin K, thiamin, riboflavin, niacin, vitamin $B_6$, folic acid, vitamin $B_{12}$, biotin, and pantothenic acid, taurine, DL-methionine, and a mineral selected from dicalcium phosphate, potassium chloride, calcium carbonate, sodium chloride, potassium chloride, choline chloride, magnesium oxide, zinc oxide, ferrous sulfate, manganese oxide, copper sulfate, calcium iodate, and sodium selenium.

A method of making a hypoallergenic semi-solid pet food composition can further comprise heating the mixture in a vessel at a temperature of to about 65° C. (about 150° F.), or, in some configurations, to about 96° C. (about 205° F.). In various configurations, the mixture can be packaged, and subjected to further heating, to a temperature of at least about 116° C. (about 240° F.) to about 132° C. (about 270° F.), or, in some aspects, to a temperature of about 123° C. (about 254° F.). In some aspects, the latter heating can be heating sufficient to sterilize the mixture, or sufficient to generate a packaged pet food formulation, such as a canned pet food formulation, which can be shelf-stable for at least about six months, at least about one year, or at least about two years.

In various embodiments, the present teachings disclose methods for mitigating food allergy symptoms in an animal. The methods can comprise feeding to the animal a hypoallergenic pet food composition comprising a hydrolysate in a formulation described herein, such as a semi-solid formulation. In various configurations, the animal can be a companion animal, such as, in non-limiting example, a domestic dog or a domestic cat. In some aspects, mitigating food allergy symptoms in the animal can comprise feeding the animal a hypoallergenic pet food described herein to the exclusion of, in addition to, or as a partial replacement of, other food compositions. In some configurations, mitigating food allergy symptoms in an animal can comprise feeding the animal a combination of a solid food and a hypoallergenic composition described herein.

In various embodiments, the present teachings disclose methods for providing to a consumer, a shelf-stable hypoallergenic pet food composition. In various configurations, the methods can comprise providing in a container a hypoallergenic pet food composition comprising a hydrolysate and at least about 15% by weight water, and selling the pet food composition to the consumer. In some configurations, the container can be an airtight container, and in certain aspects, the airtight container can be a metal can. In these embodiments, the hypoallergenic pet food composition can comprise water in an amount of at least about 15% by weight, at least about 20% by weight, at least about 40% by weight, at least about 60% by weight, at least about 70% by weight, or at least about 80% by weight. In certain aspects, the water content can be at least about 75% by weight to about 80% by weight. In various configurations of these embodiments, the hydrolysate content of a hypoallergenic pet food can be in an amount of from about 0.5% by weight hydrolysate to about 85% by weight hydrolysate, from about 4% by weight hydrolysate to about 30% by weight hydrolysate, from about 4% by weight hydrolysate to about 14% by weight hydrolysate, from about 6% by weight hydrolysate to about 14% by weight hydrolysate, or from about 55% by weight hydrolysate to about 65% by weight hydrolysate on a dry matter basis. In various configurations of these embodiments, a shelf-stable hypoallergenic pet food can comprise a composition palatable to an animal such as a pet animal. In these configurations, palatability can be palatability determined in a competitive test with a control hypoallergenic pet food, which can be a hypoallergenic pet food composition comprising a non-hydrolyzed protein as a major protein nutrition source, or a hypoallergenic pet food composition comprising powdered hydrolysate as a major protein nutrition source. Palatability, in these configurations, can be palatability having an intake ratio of at least about 0.5 when tested against at least one control pet food. In various configurations of these embodiments, a shelf-stable hypoallergenic pet food composition can have a shelf stability of at least about six months, a shelf stability of at least about one year, or a shelf stability of at least about two years.

The present inventors have developed pet food compositions which are hypoallergenic to companion animals and are in semi-solid formulations.

Component amounts are reported herein in terms of weight percentage (% by weight), i.e. weight of a component reported as a fraction of total weight of a composition. As used herein, a "semi-solid formulation" is a mixture which comprises greater than about 15% by weight water, yet flows slowly, if at all, under ambient conditions of temperature and external force such as gravity. A semi-solid formulation of the present teachings can substantially retain the shape of its container (such as a metal can) under ambient conditions. In various configurations, a semi-solid formulation can be easily divided by a consumer with the aid of a common dining utensil such as a fork, a spoon or a knife. A semi-solid formulation can have a density, texture and firmness akin to that of a conventional canned loaf pet food, a pat or a mousse. In various configurations, a semi-solid formulation can have the density, texture and firmness of a gravy, a gel, a hash, a purée, or a semi-moist pet food formulation, but not that of a gruel. Components of a semi-solid formulation of the present teachings can have a homogeneous texture, or a heterogeneous texture. A semi-solid formulation can comprise fibrous material. A semi-solid formulation can be, for example, a colloid, a gel, or a gum.

"Hypoallergenic", as used herein, describes a composition comprising a hydrolysate, or the hydrolysate itself, which, when administered to a subject animal, evokes less allergic response than a comparable composition containing non-hydrolyzed protein. In some configurations, no allergic response is detected following administration of a hypoallergenic formulation.

Allergenicity, including hypoallergenicity, can be measured and quantified for a formulation using any method known to skilled artisans, such as, in non-limiting example, conducting an ELISA assay or an immunoprecipitation assay in which an IgE response is measured in a serum sample of an animal administered a composition. Allergenicity can also be determined by direct observation, such as, for example, observation of an animal by its owner, caregiver or veterinarian. In these configurations, the owner, caregiver or veterinarian determines allergenicity by observing the severity of symptoms associated with food allergies in the subject animal, in accordance with principles and standards of animal care and treatment which are well known in the art.

A hypoallergenic pet food composition of the present teachings can comprise a hydrolysate. "Hydrolysate," as used herein, means a chemically heterogeneous mixture comprising polypeptides and free amino acids wherein at least 85% of the amino acid content is comprised by oligopeptide chains, polypeptide chains having a molecular weight of less than about 18 kilodaltons (kD), and free amino acids. The term "polypeptide," as used herein, can include an amino acid chain of any length, including oligopeptides, dipeptides, tripeptides, and larger peptides. A hydrolysate of a hypoallergenic food composition herein can be a source of protein nutrition. The term "hydrolysate" as used herein describes a mixture of amino acids and polypeptide chains, regardless of the method of its production. Hence, a hydrolysate can be produced by any known chemical or enzymatic method, such as, in non-limiting example, methods disclosed in U.S. Pat. No. 5,589,357 to Martinez, U.S. Pat. No. 4,879,131 to De Rahm, U.S. Pat. No. 5,039,532 to Jost, or European Patent EP001236405 to Fritsche. A hydrolysate can also be prepared by chemical synthesis, for example through synthesis of random peptide polymers using free amino acids and a coupling reagent such as 1-ethyl-3-(3-dimethylaminopropyl)carbodiimide.

Hypoallergenic pet food compositions of the present teachings can include both "low allergen" and "ultra-low allergen" configurations. The latter can include a hydrolysate as the source of at least about 95% of protein nutrition, at least about 99% of protein nutrition, or 100% of protein nutrition, while the former can include, in addition to hydrolysate, some non-hydrolyzed protein of low allergenicity, such as, for example, plant protein such as soy bean protein, as a source of protein nutrition. As used herein, the terms "protein nutrition" and "protein nutrient" means any protein(s), polypeptide(s), oligopeptide(s), free amino acid(s), or combinations thereof, which can serve as a source of amino acids. For example, a protein hydrolysate which lacks any full-length protein and comprises only oligopeptides and free amino acids can be a source of protein nutrition.

As used herein, the term "frozen hydrolysate" means a hydrolysate that is frozen, rather than desiccated or powdered, following its production. A "composition comprising a frozen hydrolysate" (and similar terms) indicates that a frozen hydrolysate is used in the preparation of the composition. However, such terms can encompass a frozen hydrolysate that is thawed before formation of a composition.

In some configurations, a hydrolysate used in the pet food compositions herein can comprise free amino acids and polypeptides heterogeneous in size, in which at least about 99% are less than about 50,000 Daltons. A hydrolysate used in some configurations of the pet food compositions herein can comprise a heterogeneous collection of polypeptides and free amino acids of which no greater than about 10% by weight have a molecular weight of about 10,000 Daltons or greater. In some embodiments of the present invention, the polypeptides and free amino acids which comprise a hydrolysate can have a weight average molecular weight, a number average molecular weight, a Z-average molecular weight or a viscosity average molecular weight of no greater than about 2,000 Daltons, no greater than about 4,000 Daltons, no greater than about 6,000 Daltons, no greater than about 8,000 Daltons, no greater than about 10,000 Daltons, no greater than about 12,000 Daltons, or no greater than about 18,000 Daltons. Molecular weight of a hydrolysate or components thereof, including an average molecular weight such as a weight average molecular weight, can be determined using any method known to skilled artisans. In non-limiting example, molecular weight distribution of polypeptides comprised by a hydrolysate can be determined using size exclusion chromatography in a medium such as Sephadex® (Pharmacia), or gel electrophoresis using SDS-polyacrylamide gel electrophoresis, using methods well known to skilled artisans. In certain embodiments of the present teachings, a hypoallergenic pet food composition can comprise a hydrolysate which comprises polypeptides and free amino acids in which about 60% to about 95% of the polypeptides and free amino acids have a molecular weight below about 6,000 Daltons, below about 8,000 Daltons, below about 10,000 Daltons, below about 12,000 Daltons, or below about 15,000 Daltons. In various configurations, a hydrolysate used in a pet food composition herein can comprise a plurality of polypeptides and free amino acids in which from about 80% to about 95% of the polypeptides and free amino acids have a molecular weight below about 6,000 Daltons. In various configurations, a hydrolysate used in a pet food composition herein can comprise a plurality of polypeptides and free amino acids in which at least about 90% of the polypeptides and free amino acids have a molecular weight below about 3,000 Daltons.

A hydrolysate used in a pet food of the present teachings can be a hydrolysate prepared using methods known to skilled artisans. In non-limiting example, a hydrolysate used herein can be a hydrolysate prepared by treating a biological source of protein nutrients with one or more enzymes such as a protease, for example trypsin or chymostrypsin; one or more non-enzyme chemical reagents, such as an acid, for example acetic acid; or some combination thereof. In non-limiting example, a method for forming a hydrolysate can be a method disclosed in U.S. Pat. No. 5,589,357, U.S. Pat. No. 4,879,131, U.S. Pat. No. 5,039,532, U.S. Pat. No. 6,403,142, U.S. Pat. No. 6,589,574, U.S. Pat. No. 6,455,273, US Patent Application 2003/0035882 A1, or European Patent EP 1 236 405 A1.

In various configurations, the hydrolysate can be a frozen hydrolysate. Use of the frozen hydrolysate in the preparation of a pet food of the present teachings can yield a pet food having enhanced organoleptic acceptability or palatability compared to a pet food prepared using a dried hydrolysate but otherwise prepared substantially identically, for example as shown below in Example 1.

In certain configurations, a hydrolysate can comprise other chemical substances in addition to polypeptides and free amino acids, such as, for example, biochemicals such as lipids, fats, oils, vitamins and carbohydrates. In some configurations, substances comprising a hydrolysate can be components derived from the biological material used to generate the hydrolysate, or can be chemical substances added by a hydrolysate manufacturer. These substances can be, in non-limiting example, a carbohydrate such as sucrose, tapioca starch, corn sweetener, cornstarch, a partially hydrolyzed starch, cellulose, or a partially hydrolyzed cellulose. Some other non-limiting examples of components that can be comprised by a hydrolysate are organic oils, such as soybean oil, safflower oil, palm oil, coconut oil, sunflower oil, peanut oil or canola oil.

In various embodiments, a biological material including polypeptides which can be used to prepare a hydrolysate for a pet food composition described herein can be from animal protein such as, in non-limiting example, mammalian protein, avian protein, reptilian protein, amphibian protein, fish protein, invertebrate protein or combinations thereof. In non-limiting example, a mammalian protein source can be cattle, sheep, pig, goat, deer, rabbit, horse, kangaroo, their milk, curds, whey or blood, and internal tissues and organs such as smooth muscle, striate muscle, liver, kidney, intestine or heart; an avian protein source can be chicken, turkey, goose, duck, ostrich, quail, pigeon, their eggs and internal tissues and organs such as smooth muscle, striate muscle, liver, kidney, intestine or heart; an amphibian source can be frog or salamander; a reptile protein source can be alligator, lizard, turtle or snake; a fish protein source can be catfish, herring, salmon, tuna, bluefish, cod, halibut, trout, swordfish and their eggs; and an invertebrate protein source can be lobster, crab, clams, mussels or oysters, and combinations thereof.

In various embodiments, a biological material including polypeptides which can be used in a hydrolysate can be from a plant protein source such as, in non-limiting example, a legume, an alga, a grain and combinations thereof. In non-limiting example, some plant sources of protein for a hydrolysate can be soy, peas, beans, alga, flax seed, corn, wheat, oats, sorghum, kelp, barley, alfalfa, rye, quinoa, peanut, rice, potato and combinations thereof.

In certain embodiments, a hydrolysate can comprise hydrolyzed protein from a source selected from the group consisting of chicken, poultry liver, yeast, soy and combinations thereof.

In various embodiments, biological material including polypeptides which can be used in a hydrolysate can be from a microbial source such as, in non-limiting example, bacteria such as *Escherichia coli*, or yeast such as *Saccharomyces cerevisiae*.

In various embodiments, the hypoallergenic pet food compositions described herein can have a water content greater than that of solid format pet foods such as kibble, which typically have a water content no greater than about 12% by weight. In various embodiments, a pet food composition of the present teachings can have a water content of at least about 15% by weight, at least about 20% by weight, at least about 40% by weight, at least about 60% by weight, at least about 70% by weight, or at least about 80% by weight. In certain aspects, the water content can be at least about 75% by weight to about 80% by weight. In addition, in various embodiments, a hypoallergenic pet food compositions can comprise a hydrolysate in an amount of from at least about 0.5% by weight to about 85% by weight. As used herein, the weight content of any non-water component of any formulation is the dry weight. In illustrative example, a 100 gram sample of a pet food composition comprising 1% by weight hydrolysate contains 1 gram of dry hydrolysate. Dry weight of a hydrolysate can be determined, in non-limiting example, by desiccating a sample of the hydrolysate, and weighing the dried sample on an analytical balance. In some configurations, the hydrolysate content of a hypoallergenic pet food can be at least about 4% by weight hydrolysate to about 70% by weight hydrolysate, at least about 4% by weight hydrolysate to about 14% by weight hydrolysate, at least about 6% by weight hydrolysate to about 14% by weight hydrolysate, or at least about 55% by weight hydrolysate to about 65% by weight hydrolysate.

In various configurations, a hypoallergenic pet food of the present teachings can be a "nutritionally complete" diet for a companion animal such as a dog or cat. A "nutritionally complete" diet can be a diet that includes all nutrients required for maintenance of normal health of a subject animal. Accordingly, pet foods disclosed herein can be nutritionally complete for a dog or for a cat.

In various embodiments, a hypoallergenic pet food can comprise a palatable pet food composition. A palatable hypoallergenic pet food composition of these configurations can be a pet food in a format such as, in non-limiting example, a semi-solid format, a liquid format, for example a slurry, a gravy, a gel, a hash, a purée, or a semi-moist pet food formulation format, but not a gruel. In certain configurations, palatability of a pet food composition can be enhanced by the inclusion in a pet food composition of a hydrolysate which, unlike powdered or other dried hydrolysates, has not been subjected to desiccation. In some configurations, the hydrolysate comprised by a hypoallergenic pet food can be a frozen hydrolysate. Desiccated hydrolysates, which are supplied commercially as powdered hydrolysates and can have a water content less than about 10% by weight, typically can involve preparation that comprises evaporation, heating in an oven to a temperature of at least about 90° C. (192° F.), and/or spray drying. Without being limited by theory, it is believed that subjecting a hydrolysate to a desiccation process can cause the hydrolysate to lose much of its palatability. Accordingly, a hypoallergenic pet food comprising a dried hydrolysate can be less palatable to an animal than a similar hypoallergenic pet food comprising a frozen hydrolysate. Accordingly, in some configurations, the hydrolysate comprised by a hypoallergenic pet food can be a frozen hydrolysate.

In various embodiments, a semi-solid hypoallergenic pet food of the present teachings can be prepared using a hydrolysate that has not been dried or formed into a powder. Accordingly, a pet food composition of various configurations of the present teachings can comprise a hydrolysate that is frozen after it is generated. A hydrolysate that is frozen after it is generated can maintain or enhance its palatability. Furthermore, a pet food composition of various embodiments of the present teachings can comprise a hydrolysate that is incorporated fresh into a pet food formulation directly after it is generated, or refrigerated after it is generated. Without being limited by theory, it is believed that a hypoallergenic pet food comprising a frozen hydrolysate can be more palatable to an animal than a hypoallergenic pet food comprising a dried hydrolysate.

Accordingly, a pet food composition of the present teachings can have a palatability that is enhanced in comparison to a control pet food composition. Enhanced palatability can be quantified by determining an intake ratio in a palatability test. In one type of competitive palatability test, a test pet food such as a pet food formulation of the present embodiments is offered individually to test animals (dogs or cats). Each test animal receives a pre-weighed food dish containing the test pet food formulation, and, simultaneously, a pre-weighed food dish containing a comparator pet food formulation, such as, for example, a hypoallergenic wet format pet food. The food dishes are left with the animal for a predetermined duration (45 minutes for a dog, 16 hours for a cat). At the end of the predetermined time interval, the food dishes are removed and re-weighed, and the intake amount of each formulation can be determined. An intake ratio (IR) can then be determined using the formula $IR=A/(A+B)$, wherein A=the amount of test formulation consumed by the animal, and B=the amount of comparator formulation consumed by the same animal, averaged over a pre-determined duration. In various embodiments, the comparator formulation for a palatability test can be a "wet food" composition comprising the formulation set forth in Table 1. A pet food comprising a composition of the present teachings can yield an intake ratio of at least about 0.20, at least about 0.25, at least about 0.3, at least about 0.4, or at least about 0.5, when tested against the formulation described in Table 1.

TABLE 1

| Ingredient | % (by weight) of Composition |
|---|---|
| Water | 54.2 |
| Rice, Parboiled Broken Milled | 16.3 |
| Lamb Trim | 14 |
| Liver, Lamb | 8.5 |
| Rice Flour, Cellulose RM, Red Iron Oxide Sltn, Soybean Oil (Crude Degummed), Calcium Carbonate, Salt, Iodized, Potassium Chloride, Dicalcium Phosphate, Mineral Mix, Vitamin Premix, Taurine | 7 |

In certain configurations, other competitive consumption tests can be used to determine palatability of a pet food of the present teachings. In certain configurations, consumption of a pet food can be scored against a control formulation which is a hypoallergenic pet food comprising non-hydrolyzed protein as its major protein nutrition source. In these configurations, the palatability score for a semi-solid composition taught herein can be at least about IR=0.5, IR=0.6, IR=0.7, or IR=0.8. In another palatability test, a composition of the present teachings can be scored against a hypoallergenic solid format pet food comprising powdered hydrolysate as its major protein nutrition source. In these configurations, the palatability score for a semi-solid composition taught herein can be at least about IR=0.5, at least about IR=0.6, at least about IR=0.7, or at least about IR=0.8.

In various embodiments, organoleptic acceptability of pet foods described herein can be measured in cross-over tests of palatability. In these tests, two formulations can be tested on a population of dogs. The population can be divided into two groups. For days 1-5 of a cross-over study, a first group is fed a first formulation and a second group is fed a second formulation. On days 6 and 7, the distribution of formulations are crossed-over so that those dogs who were receiving the first formulation now receive the second formulation, and vice versa. Each daily feeding can last for 45 minutes, and animals can eat ad libitum during the feeding. Consumption by the animals of the cross-over formulations during the final days can be determined by weighing feed dishes as described supra. Consumption can then be compared, and analyzed statistically using standard statistical tests such as a Student's T-test. A statistically significant preference can have a P-value of less than 0.05. Results from these studies on hypoallergenic food formulations having acceptable stool ratings are presented in an example below.

In various embodiments, organoleptic acceptability of pet foods described herein can be measured by measuring intake of a pet food under test conditions. In various configurations, a hypoallergenic pet food of the present teachings can be a hypoallergenic pet food which is consumed by pet animals in sufficient quantity to provide at least minimum required calories on a daily basis. A sufficient quantity can be, for example, an amount that supplies to a dog which ingests the pet food, at least about 112 kcal per kilogram of metabolic body weight of the dog. In non-limiting example, a beagle weighing 50 lbs. can consume at least about 1166 kcal of a hypoallergenic pet food described herein on a daily basis.

In various configurations, acceptability of pet food compositions described herein can be analyzed using canine stool test. In these tests, study dogs are weighed at the beginning and end (days 1 and 8) of the study. The dogs should maintain their beginning weight. Stools are rated daily on a scale of 1-5 for acceptability, wherein a rating of "5" is considered the most acceptable. The data is analyzed to provide "fecal scores" from the stool ratings, and daily intake of food is also measured. Only healthy, adult dogs are used for the study and administered no pharmaceuticals or other drugs during the study. Daily intake of an animal, daily fecal score of an animal, average intake of an animal, and average daily fecal score of animal can all be recorded; and a frequency histogram of fecal scores can be generated. A stool rating wherein at least about 80% of stools examined have a rating of "5" is considered acceptable for a pet food formulation. Results from these studies on hypoallergenic food formulations having acceptable stool ratings are presented in an example below.

In certain configurations, a hypoallergenic pet food composition can be a shelf-stable pet food composition. A shelf-stable pet food composition, as used herein, means a pet food composition which, upon storage at ambient conditions, retains its suitability for its intended use for at least about six months, for at least about one year, or for at least about two years. In these configurations, the pet food composition can be packaged in a container such as an airtight container, which can be, in non-limiting example, a retort pouch, a tetra pack, a bottle, a tray, or a metal can such as a tin can. In some configurations, the composition is packaged in a sterile condition. In these configurations, the pet food can be stable until its container is opened. In various embodiments, shelf stability can be achieved using methods well known to skilled artisans, such as, in non-limiting example, thermal sterilization, non-thermal sterilization, retort processing, aseptic processing, UHT, and/or high pressure.

In various configurations of the present teachings, a hypoallergenic pet food can comprise, in addition to a hydrolysate and water, one or more supplemental components. These supplemental components can, in some configurations, modify the physical characteristics of a pet food, such as, for example, the pet food's firmness or texture, and/or act as a nutritional supplement. A nutritional supplement can be, in non-limiting example, a monosaccharide, a disaccharide, an oligosaccharide, a starch such as tapioca starch or corn starch, a flour such as wheat flour, rye flour, or corn flour, a cellulose, a tuber, a grain (whole, ground or milled) selected from rice, wheat, corn and rye, a gluten such as rice gluten, a vitamin selected from vitamin A, vitamin C, vitamin D, vitamin E, vitamin K, thiamin, riboflavin, niacin, vitamin $B_6$, folic acid, vitamin $B_{12}$, biotin, and pantothenic acid, taurine, DL-methionine, and a mineral selected from calcium carbonate, sodium chloride, potassium chloride, dicalcium phosphate, sodium chloride (iodized), choline chloride, calcium sulfate dihydrate and magnesium oxide, zinc oxide, ferrous sulfate, manganese oxide, copper sulfate, calcium iodate, and sodium selenium. Some other non-limiting examples of some supplemental components also include dried potato, potato starch, soybean oil (crude degummed), and cellulose. In some configurations, a nutritional supplement can be protein of low allergenicity, such as, for example, plant protein such as soy bean protein.

In some embodiments, the present teachings include methods of making a hypoallergenic pet food. In various embodiments, these methods can include methods of improving the palatability of a hypoallergenic pet food composition, by preparing the pet food composition using a frozen hydrolysate. In various configurations of these embodiments, the improved palatability can be palatability compared to that of an identical composition prepared using a dried hydrolysate. A hypoallergenic pet food that can be made using the methods of these embodiments can comprise, in various configurations, a semi-solid composition, a liquid composition, a paste composition, a slurry composition, a gravy composition, a gel composition, a hash composition, a purée composition, or a semi-moist pet food formulation format composition, but not a gruel composition. A method of making a hypoallergenic pet food in these embodiments can comprise forming a mixture comprising a hydrolysate, and at least about 15% by weight water. In various configurations, the hydrolysate can be a frozen hydrolysate. The methods can further comprise grinding the frozen hydrolysate. In certain aspects, forming a mixture can comprise combining the components of the mixture. In various configurations, the mixture can comprise at least about 20% by weight water, at least about 40% by weight water, at least about 60% by weight water, or at least about 80% by weight water. In some aspects, the grinding can occur prior to combining the frozen hydrolysate with the water.

In various configurations, a mixture can comprise a frozen hydrolysate in an amount of from at least about 0.5% by weight, to about 85% by weight, at least about 4% by weight to about 60% by weight, at least about 4% by weight to about 14% by weight, at least about 6% by weight to about 14% by weight, or at least about 55% by weight to about 65% by weight hydrolysate on a dry matter basis. As used herein, weight reported on "a dry matter basis" means dry weight as a percentage of total weight. In illustrative example, a weight of a component of a mixture reported as "4% by weight on a dry matter basis" can be used to describe a 25 gram sample of the mixture comprising 1 gram of the component exclusive of any water content of the component.

In various embodiments, a method of making a hypoallergenic semi-solid pet food composition can further comprise adding to the mixture one or more supplemental components such as nutritional supplements described supra.

In various aspects, the methods can include cutting, chopping, or grinding solid components of the composition, with or without aqueous components present. Components can be mixed together to form a mixture, concurrent with or temporally separate from the cutting, chopping or grinding. Methods of making a hypoallergenic semi-solid pet food composition can further comprise heating a mixture in a vessel at a temperature of to about 65° C. (about 150° F.), or, in some configurations, to about 96° C. (about 205° F.). In various configurations, the mixture can be packaged, and subjected to further heating, to a temperature of at least about 116° C. (about 240° F.) to about 132° C. (about 270° F.), or, in some aspects, to a temperature of about 123° C. (about 254° F.). In some aspects, the heating can be heating sufficient to sterilize the mixture.

In some configurations of these methods, a composition can be made by batch processing. In these embodiments all ingredients, including hydrolysate in frozen block form, can be added to an agitating kettle. The ingredients can be heated to 4° C.-93° C. (40-200° F.). The product can then be packaged, and placed in a retort at 123° C. (254° F.) for 18-74 minutes.

In some configurations of these methods, a composition can be made by continuous processing. In these embodiments the ingredients can be added to a continuous cooking unit with or without controlled temperature zones, cooked from temperatures between 4° C.-96° C. (40-205° F.), with or without cycling time (reverse, forward, pause), with an agitation system moving between 1-65 rpm. The product can then packaged and placed in a retort at 123° C. (254° F.) for 18-74 minutes.

In various embodiments, the present teachings disclose methods for mitigating food allergy symptoms in an animal. As used herein, "mitigating food allergy symptoms" can mean reducing severity of food allergy symptoms in an animal diagnosed with a food allergy, or preventing development or exacerbation of such symptoms. Methods of these embodiments can comprise feeding to an animal a hypoallergenic pet food composition comprising a hydrolysate in a formulation described herein, such as a semi-solid formulation. In various configurations, the animal can be a companion animal, such as, in non-limiting example, a domestic dog or a domestic cat. In some aspects, mitigating food allergy symptoms in the animal can comprise feeding the animal a hypoallergenic pet food described herein to the exclusion of, in addition to, or as a partial replacement of, other food compositions. In some configurations, mitigating food allergy symptoms in an animal can comprise feeding the animal a combination of a solid food and a hypoallergenic composition described herein.

In various embodiments, the present teachings disclose methods for providing to a consumer, a shelf-stable hypoallergenic pet food composition. In various configurations, the methods can comprise providing in a container a hypoallergenic pet food composition comprising a hydrolysate and at least about 15% by weight water, and selling the pet food composition to the consumer. In some configurations, the container can be an airtight container, and in certain aspects, the airtight container can be a metal can. In these embodiments, the hypoallergenic pet food composition can comprise water content of at least about 15% by weight, at least about 20% by weight, at least about 40% by weight, at least about 60% by weight, to about 80% by weight. In some configurations, the water content can be from about 75% by weight to about 78% by weight. In various configurations of these embodiments, the hydrolysate content of a hypoallergenic pet food can be in an amount of from about 0.5% by weight hydrolysate to about 85% by weight hydrolysate, from about 4% by weight hydrolysate to about 30% by weight hydrolysate, from about 4% by weight hydrolysate to about 14% by weight hydrolysate, from about 6% by weight hydrolysate to about 14% by weight hydrolysate, or from about 55% by weight hydrolysate to about 65% by weight hydrolysate. In various configurations of these embodiments, a shelf-stable hypoallergenic pet food composition can be a composition palatable to an animal such as a pet animal. In these configurations, palatability can be palatability determined in a competitive test with a control hypoallergenic pet food, which can be a hypoallergenic pet food composition comprising a non-hydrolyzed protein as a major protein nutrition source, or a hypoallergenic pet food composition comprising powdered hydrolysate as a major protein nutrition source. Palatability, in these configurations, can be palatability having an intake ratio of at least about 0.5 when tested against at least one control pet food, as described supra. In various configurations of these embodiments, a shelf-stable hypoallergenic pet food composition, if contained within a sealed container such as a metal can, can have a shelf stability of at least about six months, a shelf stability of at least about one year or a shelf stability of at least about two years.

EXAMPLES

The following examples are merely illustrative, and not limiting to this disclosure in any way. All percentages in these examples are weight percentages unless otherwise indicated.

Example 1

This example illustrates several suitable hydrolysate-containing hypoallergenic pet food compositions of this invention.

Typical canine diet compositions exemplifying the present invention can contain from about 60% to about 80% water by weight, from about 10% to about 15% carbohydrate by weight, from about 10% to about 15% fat by weight, and from about 4% to about 10% hydrosylate by weight, along with other ingredients, such as calcium carbonate, cellulose, choline chloride (60%), non-hydrolyzed vegetable protein, dextrose, dicalcium phosphate, DL-methionine (99% food grade), glycine, L-cysteine HCl.$H_2O$, minerals, potassium chloride, salt (iodized), soybean oil (crude degummed), taurine, vitamins, and flavorings.

Typical feline diet compositions exemplifying the present invention can contain up to about 50% water by weight, up to about 10% carbohydrate by weight, and from about 55% to about 65% hydrolysate by weight, along with other ingredients, such as calcium carbonate, calcium sulfate dihydrate, cellulose, choline chloride (60%), dicalcium phosphate, DL-methionine, minerals, potassium chloride, salt (iodized), soybean oil, taurine, vitamins, and flavorings.

Table 2 below illustrates various hydrosylate sources that have been used in dog food formulations (Examples C1-C8) and cat food formulations (Examples F1-F3).

TABLE 2

Compositions Comprising Hydrolysates

| Formula | hydrolysate source |
|---|---|
| canine: | |
| C1 | Poultry liver[1] |
| C2 | yeast[2] |
| C3 | yeast[2] |
| C4 | Meat[3] (Chicken) |
| C5 | Meat[3] (Chicken) |
| C6 | Poultry liver[1] |
| C7 | Poultry |
| C8 | Chicken liver |
| feline: | |
| F1 | Poultry liver |
| F2 | Poultry liver4 |
| F3 | Chicken liver |

[1]Formulation C1 comprised non-hydrolyzed vegetable protein, DL-methionine, and taurine, but formulation C6 did not.
[2]Formulation C2 comprised non-hydrolyzed vegetable protein, DL-methionine, and taurine, but formulation C3 did not.
[3]Formulation C4 comprised non-hydrolyzed vegetable protein and taurine, but formulation C5 did not.
4Formulation F2 was prepared using frozen hydrolysate.

Example 2

This example illustrates palatability of certain hypoallergenic pet food formulations of the present teachings, tested against the comparator formulation described supra.

In this example, various hypoallergenic pet food compositions described in Example 1 were made either by batch processing or by continuous processing. The compositions were then tested for palatability against the comparator formulation in the competitive palatability test described above, in which intake was measured at either 6 or 14 days. As shown in Table 3, the tested compositions of the present embodiments each had an intake ratio (IR) greater than 0.2 for the canine compositions for at least one measurement. These results indicate that these hypoallergenic pet food formulations all have favorable palatability ratings.

TABLE 3

| Formula | 6 day Intake ratio | *Intake | 14 day Intake ratio | *Intake |
|---|---|---|---|---|
| C1 | 0.2929 | 212 | 0.1442 | 96 |
| C2 | 0.0410 | 30 | 0.2679 | 147 |
| C3 | 0.2681 | 150 | 0.2631 | 182 |
| C4 | 0.4159 | 483 | 0.2174 | 252 |
| C5 | 0.3300 | 232 | 0.3312 | 218 |
| C6 | 0.1451 | 85 | 0.3195 | 230 |

*Average intake of test diet

Example 3

This example illustrates palatability of certain hypoallergenic pet food formulations of the present teachings, tested against commercial pet food products recommended for animals suspected of having a food allergy.

In this example, various hypoallergenic pet food compositions described in Example 1 were made either by batch processing or by continuous processing. The compositions were then tested for palatability against comparative pet foods such as commercial pet foods using the competitive palatability test described above. In palatability tests, canine hypoallergenic pet foods described in Example 1 were tested against a commercial, dry format hypoallergenic canine formula, and feline hypoallergenic pet food compositions, also described in Example 1, were tested against either a commercial, wet format feline green peas plus lamb formulation, a commercial, wet format feline green peas plus rabbit formulation, or a feline formulation prepared using a dry hydrolysate. The commercial canine formulation comprised, as major ingredients, potato, herring meal (source of fish oil), catfish, animal fat, dried beet pulp (sugar removed) and fish digest. The commercial feline green peas plus lamb formulation comprised, as major ingredients, lamb by-products, water sufficient for processing, lamb, ground peas, canola oil and natural lamb flavor. The commercial feline green peas plus rabbit formulation comprised, as major ingredients, rabbit by-products, rabbit, water sufficient for processing, ground peas and canola oil. As shown in Table 4, the tested compositions of the present embodiments each had an intake ratio (IR) of at least 0.6318 for the canine compositions, and an intake ratio of at least 0.5795 for the feline composition. These results indicate that the hypoallergenic pet food formulations described in Example 1 all have favorable palatability ratings.

TABLE 4

Palatability of Formulas Comprising Hydrolysate v. Comparative Pet Foods

| | | | Intake | |
|---|---|---|---|---|
| | Comparative pet food | Intake ratio | Formula (g) | Commercial pet food (g) |
| Canine Formula # | | | | |
| C1 | Commercial Canine | 0.9112 | 487 | 42 |
| C2 | (Wet) Formulation | 0.7349 | 439 | 135 |
| C4 | | 0.7909 | 446 | 94 |
| C5 | | 0.6898 | 364 | 167 |

TABLE 4-continued

Palatability of Formulas Comprising Hydrolysate v. Comparative Pet Foods

| | Comparative pet food | Intake ratio | Intake Formula (g) | Commercial pet food (g) |
|---|---|---|---|---|
| C6 | | 0.7559 | 423 | 112 |
| C7 | | 0.7414 | 423 | 233 |
| C8 | | 0.6318 | 509 | 309 |
| Feline Formula # | | | | |
| F1* | Feline Formulation comprising dry hydrolysate | 0.6991 | 131 | 90 |
| F2 | Commercial Feline Green Peas and Lamb Formulation | 0.5795 | 123 | 79 |
| F3 | Commercial Feline Green Peas and Rabbit Formulation | 0.6318 | 99 | 58 |

*Test formulation and control formulation were prepared with identical components, except that the former was prepared using frozen hydrolysate and the latter was prepared using dry hydrolysate.

Example 4

This example illustrates palatability of canine formulations described in Example 1, tested in a cross-over test against a commercial canine pet food product recommended for dogs suspected of having a food allergy.

In this example, various hypoallergenic canine pet food compositions of the present teachings were made either by batch processing or by continuous processing. In cross-over tests of palatability, certain canine food compositions described herein in Example 1 were tested against a comparator (as described in Table 1), following protocols described supra. In these cross-over tests, populations of 30 dogs were divided into two groups of fifteen. For each test, the first group received a test formulation described in Example 1, and the second group received a commercial, dry format hypoallergenic canine formula on days 1-5. On days 6 and 7, the distribution of food was reversed, so that the first group received the commercial, dry format hypoallergenic canine formula and the second group received the test formulation. Consumption of food on days 6 and 7 was measured, and the results compared statistically, as shown in Table 5.

TABLE 5

| Formula # | Formula Intake (grams) | Commercial Canine Diet Intake (grams) | P value |
|---|---|---|---|
| C1 | 1031 | 947 | 0.0609 |
| C2 | 1122 | 1068 | 0.1452 |
| C4 | 1098 | 1075 | 0.5058 |
| C5 | 1128 | 972 | 0.0001 |
| C6 | 1100 | 1069 | 0.4202 |

Example 5

This example illustrates acceptability of pet food compositions described in Example 1 in a canine stool test.

In this example, 10 healthy adult dogs were fed once daily over an eight day period. Each serving comprised 200 grams of a hypoallergenic pet food formulation. Stool acceptability was assessed each day of the study for each dog. Stools were rated on a scale from 1 to 5, with a score of 5 representing the most acceptable stool rating. Stool ratings for the various formulations tested are shown in Table 6.

TABLE 6

Stool Test

| | Stool Rating Percent | | | | |
|---|---|---|---|---|---|
| Formula # | 5 | 4 | 3 | 2 | 1 |
| C1 | 85.1 | 14.9 | 0 | 0 | 0 |
| C2 | 82.6 | 17.4 | 0 | 0 | 0 |
| C4 | 84.4 | 11.7 | 3.9 | 0 | 0 |
| C5 | 82.6 | 17.4 | 0 | 0 | 0 |
| C6 | 92.8 | 7.2 | 0 | 0 | 0 |

As shown in Table 6, all the formulations tested yielded a fecal stool rating of "5" for more than 80% of the samples examined. These results indicate that dogs fed the formulations described in Example 1 produced stools having acceptable ratings.

All the references cited above are incorporated by reference into this patent. Any discussion of references cited herein is intended merely to summarize the one or more assertions made by their authors. No admission is made that any reference or portion thereof constitutes relevant prior art. Applicants reserve the right to challenge the accuracy and pertinency of the cited references.

The words "comprise", "comprises", and "comprising" are to be interpreted inclusively rather than exclusively.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A method for mitigating food allergy symptoms in a dog or a cat, the method comprising feeding to the dog or cat a semi-solid hypoallergenic food composition comprising from about 4% to about 14% hydrolysate by weight on a dry matter basis, wherein the hydrolysate provides at least 95% of protein nutrition in the composition and comprises a plurality of polypeptides and free amino acids, wherein at least about 90% of the hydrolysate is made up of polypeptides and free amino acids having an average molecular weight of less than about 3,000 Daltons, wherein the hydrolysate comprises a hydrolyzed protein from a source selected from the group consisting of an animal, an alga, a grain and a yeast and wherein the composition is palatable and nutritionally complete for a dog or cat.

2. The method of claim 1, wherein the hypoallergenic food composition comprises:
at least about 15% water by weight.

* * * * *